United States Patent
Xie

(10) Patent No.: US 9,556,731 B2
(45) Date of Patent: Jan. 31, 2017

(54) IMMERSION PROBE FOR MULTI-PHASE FLOW ASSURANCE

(71) Applicant: SCHLUMBERGER TECHNOLOGY CORPORATION, Sugar Land, TX (US)

(72) Inventor: Cheng-Gang Xie, Singapore (SG)

(73) Assignee: SCHLUMBERGER TECHNOLOGY CORPORATION, Sugar Land, TX (US)

(*) Notice: Subject to any disclaimer, the term of this patent is extended or adjusted under 35 U.S.C. 154(b) by 0 days.

(21) Appl. No.: 14/540,827

(22) Filed: Nov. 13, 2014

(65) Prior Publication Data

US 2015/0136963 A1 May 21, 2015

Related U.S. Application Data

(62) Division of application No. 13/516,686, filed as application No. PCT/IB2010/003294 on Dec. 17, 2010, now Pat. No. 8,916,815.

(Continued)

(51) Int. Cl.
*E21B 49/08* (2006.01)
*G01N 21/33* (2006.01)
(Continued)

(52) U.S. Cl.
CPC ............ *E21B 49/087* (2013.01); *G01N 21/33* (2013.01); *G01N 21/3504* (2013.01);
(Continued)

(58) Field of Classification Search
CPC  G01N 21/3504; G01N 21/35; G01N 33/2823; G01N 1/405; E21B 49/08; G01J 3/28
(Continued)

(56) References Cited

U.S. PATENT DOCUMENTS 4,856,584 A * 8/1989 Seidner .................... 166/250.05
5,663,559 A   9/1997 Auzerais et al.
(Continued)

FOREIGN PATENT DOCUMENTS

GB   2406386 B   3/2007
GB   2426579 B   1/2008
(Continued)

OTHER PUBLICATIONS

International Search Report of PCT Application No. PCT/IB2010/003293 dated Aug. 18, 2011.
(Continued)

*Primary Examiner* — Marcus Taningco

(57) ABSTRACT

An immersion probe is described that includes sensing elements that allow for hydrate inhibitor dosage to be more efficiently provided into gas and/or oil wells. The immersion probe allows for detection of first appearance of water in a multiphase flow in a well, measuring the amount of inhibitor in water within the well, determining an accurate water-cut, and measuring other property such as water salinity. Accordingly, with the known water-cut, salinity and the water flow rate inferred from the inhibitor injection flow rate and inhibitor-in-water fraction, a correct dosage of the inhibitor can be injected to the well in order to prevent hydrate formation, while reducing overdosing. Water flow rate may also be inferred from an independently measured liquid flow rate and the immersion-probe measured water cut.

15 Claims, 5 Drawing Sheets

Related U.S. Application Data

(60) Provisional application No. 61/288,371, filed on Dec. 21, 2009, provisional application No. 61/288,048, filed on Dec. 18, 2009.

(51) Int. Cl.

| | | |
|---|---|---|
| *G01N 21/359* | (2014.01) | |
| *G01N 21/85* | (2006.01) | |
| *G01N 21/3504* | (2014.01) | |
| *G01N 21/3577* | (2014.01) | |
| *G01V 3/30* | (2006.01) | |
| *G01V 8/22* | (2006.01) | |
| *G01N 21/05* | (2006.01) | |
| *G01J 3/28* | (2006.01) | |

(52) U.S. Cl.
CPC ....... *G01N 21/359* (2013.01); *G01N 21/3577* (2013.01); *G01N 21/8507* (2013.01); *G01V 3/30* (2013.01); *G01V 8/22* (2013.01); *G01J 3/28* (2013.01); *G01N 21/05* (2013.01); *G01N 2201/061* (2013.01)

(58) Field of Classification Search
USPC ......................................................... 250/256
See application file for complete search history.

(56) References Cited

U.S. PATENT DOCUMENTS

| | | | |
|---|---|---|---|
| 6,041,860 A | 3/2000 | Nazzal et al. | |
| 6,292,756 B1 | 9/2001 | Lievois et al. | |
| 6,588,266 B2 | 7/2003 | Tubel et al. | |
| 6,688,180 B1 | 2/2004 | Lund et al. | |
| 6,831,470 B2 | 12/2004 | Xie et al. | |
| 7,650,799 B2 | 1/2010 | Atkinson et al. | |
| 7,717,000 B2 | 5/2010 | Xie et al. | |
| 7,804,598 B2 | 9/2010 | Hall et al. | |
| 7,942,065 B2 | 5/2011 | Xie | |
| 8,027,794 B2 | 9/2011 | Xie | |
| 2002/0066309 A1 | 6/2002 | Tubel et al. | |
| 2003/0057401 A1* | 3/2003 | Craig ............................ | 252/387 |
| 2004/0043501 A1 | 3/2004 | Means et al. | |
| 2006/0027369 A1* | 2/2006 | Baycroft et al. ............... | 166/300 |
| 2007/0114372 A1 | 5/2007 | Lievois et al. | |
| 2007/0224692 A1* | 9/2007 | Agar et al. ..................... | 436/150 |
| 2007/0284318 A1* | 12/2007 | Max ............................... | 210/774 |
| 2008/0043240 A1 | 2/2008 | Reminiac et al. | |
| 2009/0204346 A1 | 8/2009 | Xie | |
| 2009/0216463 A1 | 8/2009 | Xie et al. | |
| 2009/0229375 A1 | 9/2009 | Atkinson et al. | |
| 2010/0145634 A1* | 6/2010 | Pinguet et al. ................. | 702/45 |
| 2010/0299088 A1 | 11/2010 | Huang et al. | |
| 2010/0315645 A1 | 12/2010 | Hall et al. | |
| 2011/0027803 A1 | 2/2011 | Moussavi et al. | |

FOREIGN PATENT DOCUMENTS

| | | |
|---|---|---|
| GB | 2432425 B | 1/2008 |
| GB | 2431010 C | 5/2008 |
| GB | 2447490 B | 5/2009 |
| KR | 2009090616 A | 8/2009 |

OTHER PUBLICATIONS

Sato et al., "Hydrophobic hydration and molecular association in methanol-water mixtures studied by microwave dielectric analysis," J. Chem. Phys., 2000, vol. 112(6): pp. 2924-2932.
Cho et al., "Determination of Water Content in Ethanol by Miniaturized Near-Infrared (NIR) System," Bull. Korean Chem. Soc., 2005, vol. 26(1): pp. 115-118.
Hall et al., "Paper 5.2: Testing of the Red Eye Near-Infrared Water Cut Monitor in High GVF Multiphase Flow Conditions," 6th International South East Asia Hydrocarbon Flow Measurement Workshop, Mar. 2007: pp. 1-25.
Katsumoto et al., "Usefulness of a curve fitting method in teh analysis of overlapping overtones and combinations of CH stretching modes," J. Near Infrared Spectrosc., 2002, vol. 10: pp. 85-91.
Lin et al., "Simultaneous determination of physical and chemical properties of sodium chloride solutions by near infrared spectroscopy," J. Near Infrared Spectrosc., 1993, vol. 1: pp. 109-120.
Sato et al., "Dynamical aspects of mixing schemes in ethanol-water mixtures in terms of the excess partial molar activation free energy, enthalpy, and entropy of the dielectric relaxation process," J. Chem. Phys., 1999, vol. 110(5): pp. 2508-2521.

* cited by examiner

IMMERSION PROBE FOR MULTI-PHASE FLOW ASSURANCE

CROSS-REFERENCE TO RELATED APPLICATIONS

This application is a divisional application and claims the benefit under 35 U.S.C. §120 to U.S. application Ser. No. 13/516,686 filed Oct. 1, 2012, which is the National Stage of PCT Application No. PCT/IB2010/003294 filed Dec. 17, 2010 which claims benefit of U.S. Provisional Patent Application Ser. No. 61/288,371 filed Dec. 21, 2009 and U.S. Provisional Patent Application Ser. No. 61/288,048 filed Dec. 18, 2009, all of which are incorporated herein by reference in their entireties.

BACKGROUND

This disclosure relates in general to immersion probes and, but not by way of limitation, to immersion probes utilized for detecting the first appearance of water in a multiphase flow in a well and measuring hydrate-inhibitor fraction in water for determining proper hydrate-inhibitor injection rates within oil and gas wells for flow assurance.

In both natural gas and crude oil wells, hydrate formation can occur at low temperatures (e.g., a few degree Celsius) and high pressures. This is due to the presence of water that is co-produced within the majority of natural gas or oil producing wells. In subsea or deepwater gas wells, for example, the aforementioned conditions of low temperature and high-pressure flows are typical. Within these wells, gas hydrate, an ice-like structure of crystalline solid consisting of water and gas molecules, can form, if not inhibited by antifreeze chemical injection in long subsea flow pipelines. The detection of the onset of water and/or water breakthrough in subsea gas wells is therefore important to flag the risk of pipeline blockage by hydrate formation and hence to identify a need for injection of the correct amount of hydrate inhibitors, such as glycols and/or other types of alcohols. The detection of formation saltwater breakthrough into a well/pipeline is also important, since in such an occurrence corrosion inhibitors may be needed to be injected to prevent the saltwater corroding the pipeline and/or wellbore system. Detection of the saltwater breakthrough is also important because the presence of salt within the produced water can affect the properties of the multiphase flow of hydrocarbons influencing important multiphase flow measurements as well as the hydrate formation temperature.

To combat hydrate-formation problems, thermodynamic inhibitors are used in addition to insulated flow pipes in subsea or deepwater. These inhibitors lower the temperature and pressures at which hydrates form within the pipeline. Other inhibitors, such as low dosage hydrate inhibitors, or kinetic inhibitors, may completely diminish hydrate formation, while functioning at substantially lower temperatures and higher pressures within a well pipe. In use, the inhibitors are pumped into the well pipeline to help ensure that no crystals will form and impede flow and/or block the pipe. However, hydrate inhibitors are expensive, and pumping large amounts into the wells/pipelines greatly increases production costs. Hydrates are also thermodynamically suppressed by the presence of antifreeze materials such as salts; as such, a common practice is to introduce, for example, 20 to 23 percent by weight (wt. %) of sodium chloride (NaCl) into the well/pipeline to address hydrate issues. Hence, the detection of change in the water salinity can be used to determine the correct usage of injected hydrate inhibitors.

Lowering the amount of inhibitors used within the well/pipe is beneficial because there is less amount of unwanted chemicals in the produced gas and oil, less associated production cost, less storage facility at the well site, less amount purchased, and less separation and re-injection of the inhibitor required. Additional production costs may also be lowered, such as the labor required for handling the inhibitors and pump requirements for introducing the inhibitor to the well. In addition, large dosages of inhibitors may cause undesirable byproducts such as foam and emulsions during the pumping process.

Finding the balance between the correct inhibitor dosage for each well can be challenging, especially due to increases in water-cut and/or water flow rate over time. Providing less inhibitors while still preventing hydrate formation can allow for flow assurance in the well pipe/pipeline and also reduce the associated production costs of the well.

BRIEF SUMMARY

The present embodiments describe an immersion probe including sensing elements, which may, among other things, allow for hydrate inhibitor dosage to be more efficiently provided into natural gas and oil wells. The immersion probe allows for detection of first appearance of water in a multiphase flow in a well, measuring the amount of inhibitor in water within the well, determining an accurate water-cut, and measuring other properties such as water salinity. Accordingly, in accordance with an embodiment of the present invention, with the known water-cut, salinity and the water flow rate inferred from the inhibitor injection flow rate and inhibitor-in-water fraction, a correct dosage of the inhibitor can be injected to the well in order to prevent hydrate formation, while reducing overdosing. In certain aspects, water flow rate may also be inferred from an independently measured liquid flow rate and the immersion-probe measured water cut.

In an embodiment of the present invention, the immersion probe utilizes, in combination with an optical absorption spectroscopic measurement, a microwave and/or a terahertz (THz)-wave coaxial sensor coupled to a reflectometer in order to measure the permittivity and conductivity of the multiphase flow in the vicinity of a probe aperture. The probe aperture can be a flow gap formed into the body of the probe where an open end of the coaxial sensor is positioned. Microwaves are transmitted through the microwave coaxial sensor in contact with a flow or a gas- or liquid-enriched flow sample, and reflected back to the reflectometer. In an embodiment of the present invention, the amount of attenuation and/or phase-shift of the reflected microwaves relative to those of the incident waves can be measured in relation to the known factors such as the frequency of the originating microwaves and the permittivity and the conductivity of the mixture which, in turn, are related to the relative proportions of its constituents (e.g., water, oil, salts and hydrate inhibitors). In an embodiment of the present invention, with these measurements, both the constituents in the multiphase flow can be detected and a more precise water-cut and/or hydrate-inhibitor fraction determined.

In one embodiment, the present disclosure provides an immersion probe for use in multiphase flow in a pipe. The immersion probe includes a housing having a first end and a second end. The immersion probe also includes one or more optical conduits which carry infrared radiation from a radiation source at the first end. The immersion probe also includes one or more electromagnetic conduits that may carry microwaves to and from a second radiation source at the first end. In an embodiment of the present invention, a reflectometer contains the second radiation source and is utilized to measure the reflected microwaves.

In an aspect of the present invention, the immersion probe further includes a flow gap across which both the infrared radiation and the microwaves are transmitted. The flow gap may be adjustable, has a predetermined distance between the first end and the second end of the immersion probe and operatively engages the multiphase flow within the pipe. In an embodiment of the present invention, the immersion probe may include one or more third optical conduits that may receive at least a portion of the infrared radiation and transmit at least a portion of the infrared radiation to a first spectrometer for spectral analysis. The infrared radiation is attenuated through absorption and/or scattering by the multiphase flow in the flow gap. In one embodiment of the present invention, the multiphase flow is then analyzed through the infrared radiation attenuation determined by the first spectrometer and through the reflected microwaves by the reflectometer.

In some embodiments, the one or more infrared radiation absorptions is utilized to determine at least one of a water fraction, an oil fraction, a hydrate-inhibitor fraction, and a water salinity of the multiphase flow in the flow gap. The one or more electromagnetic conduits can include one or more microwave open-ended coaxial sensors. The probe can be utilized to measure at least one of a permittivity and a conductivity of the multiphase flow. The at least one of the permittivity and the conductivity can also be utilized to determine at least one of a water fraction, an oil fraction, a hydrate-inhibitor fraction, and a water salinity of the multiphase flow in the flow gap. In other embodiments, the one or more first optical conduits also carry ultraviolet radiation from a third radiation source and the one or more third optical conduits receive at least a portion of the ultraviolet radiation and transmit at least a portion of the ultraviolet radiation to a second spectrometer for spectral analysis. In an embodiment of the present invention, the probe can also include a reflective element for reflecting either one or both of the infrared radiation and ultraviolet radiation from the one or more first optical conduits to the one or more third optical conduits. The second data can be data related to the properties of the multiphase flow recorded at a time prior to the collection of the first data.

In another embodiment, a method is provided for controlling the dosage of a hydrate inhibitor within a well or a pipe. The method includes transmitting one or more types of radiation into a multiphase flow through a flow gap located on an immersion probe. At least a portion of the immersion probe is located at a fixed location, or at different locations by traversing, within the well or the pipe. The method further includes collecting a first data related to the properties of the multiphase flow, analyzing the first data and communicating the first data to a processor. The first data includes measurements of the one or more types of radiation reflected from the multiphase flow. The processor is configured to determine a dosage of the hydrate inhibitor from the first data and set the dosage of the hydrate inhibitor on a pump. The pump is utilized to inject the dosage of hydrate inhibitor into the well.

In some embodiments, the processor is further configured to compare the first data to a second data, monitor changes between the first data and the second data and modify the dosage of the hydrate inhibitor according to the changes in the first and the second data. The second data can include known tables relating to the absorption spectra of optical density, multi-frequency conductivity and the permittivity of water containing contaminants such as one or more of salts, hydrate inhibitors, and oils. In some embodiments, the processor is further configured to calculate a water flow rate from the first data and the dosage of the hydrate inhibitor. The data analysis can be performed by a reflectometer through microwave dielectric spectroscopy and/or one or more spectrometers through optical spectroscopy analysis. In any of the embodiments, the one or more types of radiation can include ultraviolet radiation, infrared radiation, microwave radiation and/or THz-wave radiation.

In yet another embodiment, a computer readable medium having code executable by a processor is provided. The code causes the processor to implement the method for controlling the dosage of a hydrate inhibitor within a well or a pipe, as stated above. In any of the embodiments, the pipe/pipeline may comprise a downhole well, a subsea or a surface well, or a downhole, subsea or surface production transportation pipeline, or a bypass or a sampling line of the pipeline.

Further areas of applicability of the present disclosure will become apparent from the detailed description provided hereinafter. It should be understood that the detailed description and specific examples, while indicating various embodiments, are intended for purposes of illustration only and are not intended to necessarily limit the scope of the disclosure.

BRIEF DESCRIPTION OF THE DRAWINGS

The present disclosure is described in conjunction with the appended figures.

Figure 1:
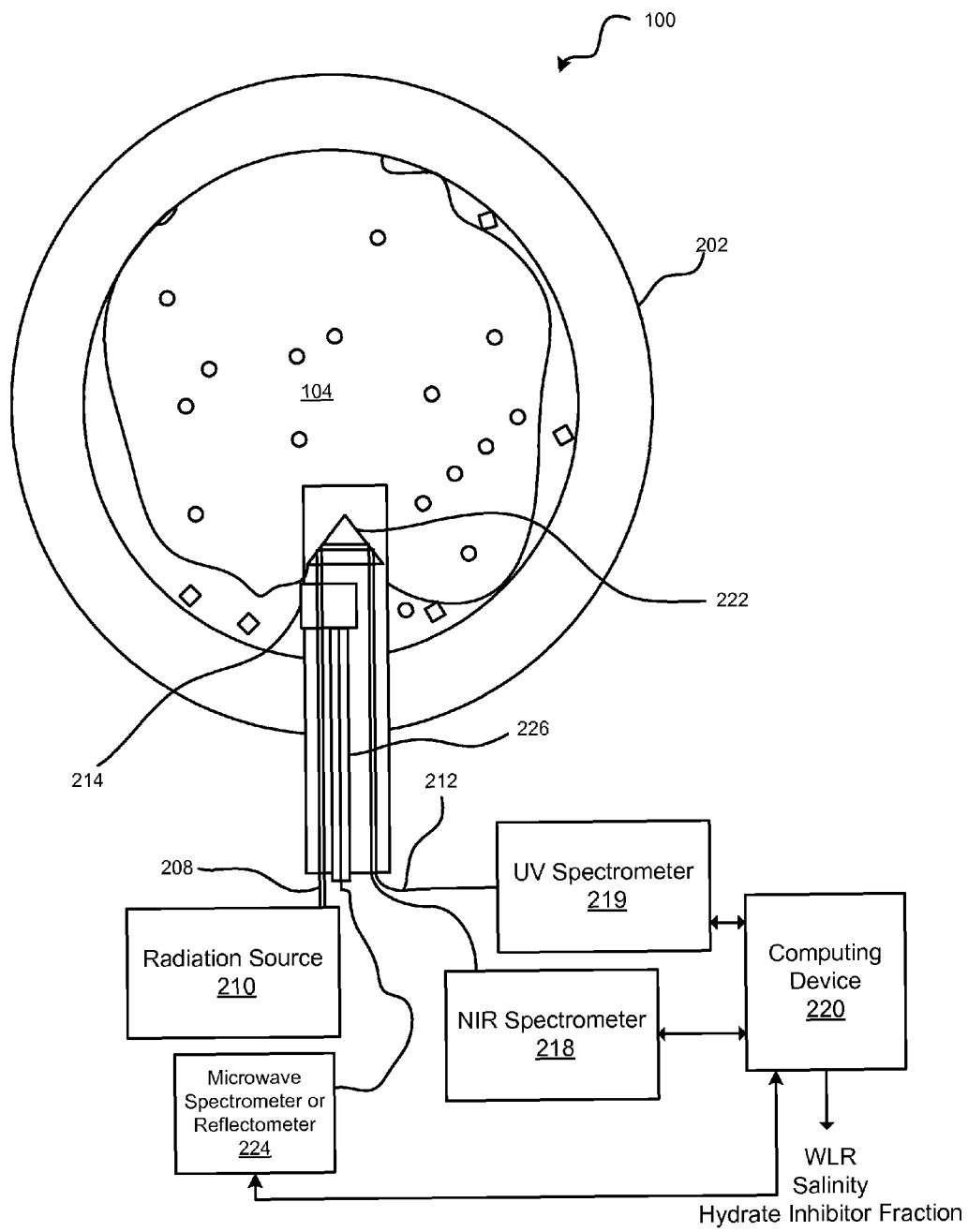
FIG. 1 provides a system for use with a combined optical and microwave immersion probe interacting with a multiphase flow, in accordance with an embodiment of the present invention.

In the appended figures, similar components and/or features may have the same reference label. Where the reference label is used in the specification, the description is applicable to any one of the similar components having the same reference label.

DETAILED DESCRIPTION

The ensuing description provides preferred exemplary embodiment(s) only, and is not intended to limit the scope, applicability or configuration of the disclosure. Rather, the ensuing description of the preferred exemplary embodiment(s) will provide those skilled in the art with an enabling description for implementing a preferred exemplary embodiment. It is understood that various changes may be made in the function and arrangement of elements without departing from the spirit and scope as set forth in the appended claims.

Immersion probes are used for measuring the water-cut of flows in well pipes through various spectroscopy techniques. By transmitting near infrared (NIR) radiation across the flow path of a probe inserted within a well pipe, the received light may be measured to determine absorption levels at different wavelengths and the determined data may then be utilized to derive the water-in-liquid ratio (WLR). In accordance with an aspect of the present invention, such immersion probes may also allow for the measurement of the WLR over a wider gas-cut range through the use of ultraviolet (UV) radiation, which UV radiation is highly absorbed by the oil condensate within the liquid phase of a multiphase flow.

In an aspect of the present invention, the combined UV/IR immersion probe allows for the amount and presence of the gas condensate, or light oil, to be measured in addition to the water in the gas-condensate well stream within the well pipe. This is because gas condensate, or light oil, is highly absorbed in the region of UV light spectrum whereas the gaseous phase and water are substantially transparent. When both the UV and IR absorptions along substantially the same/similar optical path are determined, a ratio of the volume fractions of two liquids in multiphase flow may be derived, and this ratio may be used to provide an improved measurement of the water-cut, or WLR. In an aspect of the present invention, adding UV-spectrum measurement allows for an improved optical density (absorption) contrast between the water and the gas-condensate in the multiphase flow, resulting in a WLR measurement with a much higher tolerance to scattering attenuation effects caused by liquid droplets and/or gas bubbles, especially at high gas volume fractions (GVFs) or gas cuts. This use of such UV light is further discussed in commonly owned GB patent number GB2426579B, which is hereby incorporated by reference in its entirety.

In an embodiment of the present invention, UV and NIR light sources may provide continuous light emission over a broadband spectrum of both UV and NIR light. In some aspect, the visible spectrum range may also be included in the broadband spectrum. In an embodiment of the present invention, a broadband spectrum is utilized in order to take into account the baseline shift caused by the scattering attenuation effect at multiple absorption wavelengths in addition to the changes in the absorption-peak properties of the oil and/or water at different temperatures and pressures. In an aspect of the present invention, the light sources and the spectrometers are located external to the immersion probe itself and the composite UV/NIR/Visible light may be guided from the sources through optical fiber bundles which may be coupled to an optical window within the insertion probe. The probe may include a flow gap across which the light is transmitted. In an aspect of the present invention, the light is reflected back through the probe and guided by the receiving optics and optical fiber bundles into spectrometers where spectral analysis may be performed.

In an aspect of the present invention, the immersion probe can additionally contain temperature and/or pressure sensors, which may aid in determining the flow thermodynamic conditions, measuring static and/or dynamic pressure(s), velocity, flow rates and content (e.g., solid, liquid, gas) of the mixtures within the well. In some aspects, the multiphase flow may be separated through swirling the flow and using centrifugal force to cause the flow to form a liquid annulus on the inner wall of the pipe and a gas core in the center of the pipe. The swirling technique is further discussed in the commonly owned U.S. Pat. No. 7,650,799, which is hereby incorporated by reference in its entirety. This multiphase separation is also useful for the separate measurement of flow fractions, velocities and flow rates of each phase. In an embodiment of the present invention, the pressure sensors can be located in pressure ports formed along the body of the probe in order to collect impact pressure readings for the calculation of flow rates and velocities in specified areas of the pipe.

The aforementioned immersion probes can allow for the onset of water to be detected; accurate water-cut data can be measured if the appropriate property of the water and oil phases remain the same after a calibration or the appropriate property is measured in-situ periodically. However, such immersion probes may fail to provide accurate water-cut data when a markedly different amount of hydrate inhibitor is present within the water phase of a multiphase flow. This is because the injection of inhibitors into the multiphase flow causes the absorption peaks in the IR region, particularly that of water, to vary. The hydrate inhibitors, such as methanol, glycol and/or other types of alcohols, can be readily dissolved within the water phase of the multiphase flow.

In an embodiment of the present invention, the immersion probe can additionally include a microwave open-ended coaxial sensor to detect the onset of water and to measure the inhibitor content within the water phase of the mixture, as well as to determine the water salinity. At frequencies below 1 gigahertz, an alcoholic-type hydrate inhibitor such as methanol has a dielectric-constant around 30, fresh water has a dielectric-constant around 80, and oil has a dielectric-constant around 2.2. The microwave coaxial sensor may comprise an open-ended probe designed to gather the permittivity-conductivity data of the multiphase flow through reflection-coefficient sensing methods. The water IR absorption peaks, for example one at around 1450 nm wavelength, are also sensitive to the presence of hydrate-inhibitor in water (since both include O—H bonds). In an embodiment of the present invention, the combined IR and microwave data can be utilized to track the changes in the water absorption peaks due to the presence of hydrate-inhibitor in the water within the flow. The microwave coaxial sensor measurement technique and necessary hardware is further discussed in commonly owned U.S. Pat. No. 6,831,470, which is hereby incorporated by reference in its entirety. The use of the microwave open coaxial sensor may also be utilized to detect the presence of the other constituents within the water phase, based on known effects the constituents cause on the multiphase flow conductive or dielectric properties.

In addition to inhibitor presence in the water of the multiphase flow, salts such as NaCl and potassium chloride (KCl) can also be present. As previously discussed, the salts may result from formation water breakthrough, such as may occur in deep water/subsea oil or gas wells. The addition of salt into the water phase can beneficially decrease the tendency of hydrate formation, while also offsetting the water absorption peak measurements taken with the immersion probe having NIR and/or UV capabilities. In comparison to the inhibitors, this offset due to salinity change is less profound, though still apparent. In an embodiment of the present invention, the microwave coaxial sensor has a much higher sensitivity to changes in the water conductivity and hence is suitable in detecting salinity changes.

At some concentrations, water salinity and inhibitor presence may equally offset the IR absorption peak of the water phase. As such, in an aspect of the present invention, to retrieve a correct water-cut measurement, the water phase is properly decoupled from the other aqueous components of the multiphase flow such as the salt, inhibitors, oil condensate and/or crude oil in order to take into account the IR absorption peak offsets.

Referring now to FIG. 1, a system 100 having a combined immersion probe within a well pipe is illustrated, in accordance with an embodiment of the present invention. In addition to flow pressure and/or temperature measurements (not shown), the immersion probe may effectively measure the water-cut, salinity and hydrate-inhibitor fraction of a multiphase flow 104 across a flow gap 214. The immersion probe may be inserted into a pipe 202 containing different constituents which comprise the multiphase flow. In addition, the immersion probe may be useful, for example, in deep-sea wells that utilize surface level methanol, glycol or other alcohol injection in order to inhibit hydrate formation and provide a treatment process with increased flow assurance. The immersion probe includes one or more optical radiation sources 210, such as in the range of NIR and UV. As referenced herein, the terms radiation, light, light source, light beam and any combination thereof may be utilized interchangeably. In one embodiment, an NIR and/or UV light source 210 may be directed across the flow gap 214 within the immersion probe through an optical conduit 208, such as an optical fiber bundle, which may be treated to transmit efficiently NIR and/or UV light. The light is reflected by a reflective element 222, such as a prism, mirror, white tile, or similar reflective material and collected by a receiving optical fiber bundle. The reflected light is then sent to an NIR and/or UV spectrometer 218, 219 and transferred to a computing device 220 where further spectral analysis can be performed to determine water-cut or water-in-liquid ratio (WLR) of the multiphase flow 104 in pure water (i.e., water without other constituents).

However, in multiphase flows 104 containing marked amounts of other constituents such as hydrate inhibitors, salts and similar known chemicals in wells, the aforementioned water-cut calculation may be affected. This is because some constituents cause the same attenuation in the O—H band (i.e., water) IR absorption peak magnitude. For example, at 25° C., a 20% NaCl and water mixture and a 20% methanol (i.e., inhibitor) and water mixture each cause a similar absorption in the measured water peak magnitude in the NIR range. These similarities can cause the miscalculation of the contents in the multiphase flow. Accordingly, in accordance with an embodiment of the present invention, the presence of an inhibitor is detected in order to provide more accurate water-cut calculations on the multi-phase flow. By detecting the presence of the inhibitor, effects of the inhibitor can then be factored into the calculation of the water-cut provided by the UV/IR probe.

Figure 2A:
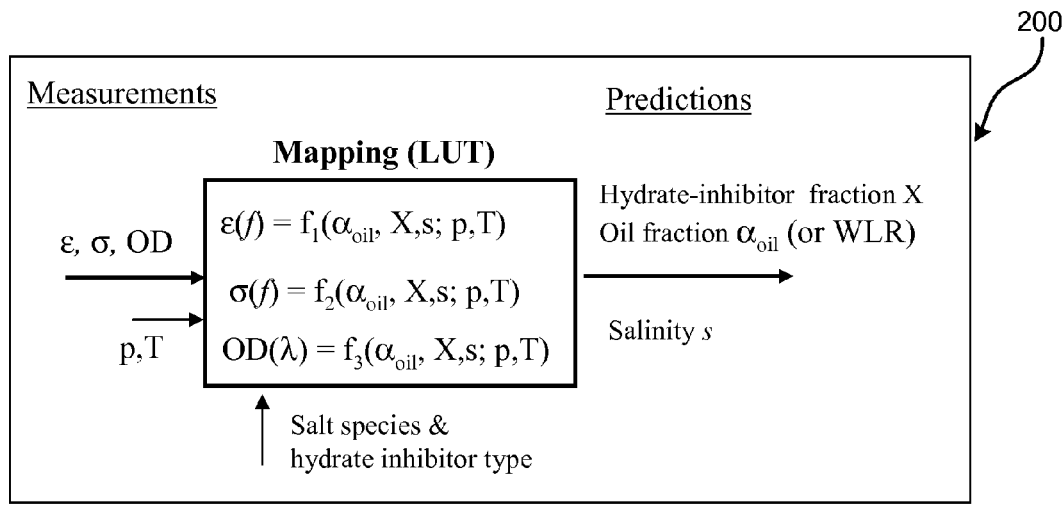
FIG. 2A provides a lookup table, in accordance with an embodiment of the present invention.

Referring now to FIG. 2A, in one embodiment, the water-cut (or WLR), hydrate-inhibitor fraction and salinity can be calculated and/or predicted through a look-up table 200 that factors in the known effects of constituents in the water phase. These look-up tables (LUT) can additionally allow for the content of the constituents to be determined through a predetermined process. In one embodiment, the look-up tables 200 include tables with measured variations in water NIR peak absorption (optical density OD) spectra over a range of wavelengths λ due to variations in water-in-liquid concentrations, temperature changes, and the presence of the aforementioned constituents. Each of the various look-up tables 200 can be referenced prior to determining the water-cut and/or the content of the constituents. For example, in some embodiments, a look-up table 200 including NIR peak absorption spectra of water containing percentages of salts can be utilized.

In certain embodiments, a look-up table 200 can be referenced that includes water absorption peak spectra of water containing each of various inhibitors, which are known to be injected within a well. In other embodiments, a look-up table including the optical absorption spectra due to temperature variations in pure water and/or water mixture containing one or more constituents (such as oil, gas) may be utilized. A combination of these embodiments can also be utilized, for example, a LUT may include a range of peak absorption spectra correlated with various levels of salinity and inhibitors over a range of temperatures. In an aspect of the present invention, having an oil-free and/or gas-free water sample allows for increased flexibility when determining the water constituents as any cross-mapping in the lookup table 200 can provide a hydrate-inhibitor fraction (X) and the salinity (s). Oil-in-water fraction ($\alpha_{coil}$) can also been included in the cross-mapping in the lookup table 200, utilizing UV peak absorption spectra containing percentages of oil and other constituents.

Figure 2B:
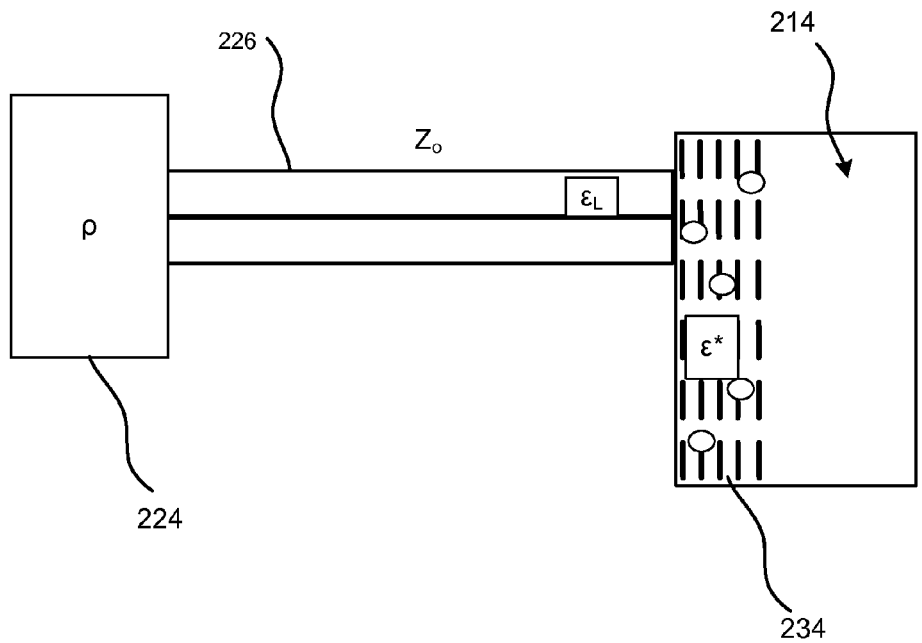
FIG. 2B provides an illustration of a microwave coaxial sensor interacting with a multiphase flow, in accordance with an embodiment of the present invention.

To determine the necessary data to reference in the lookup table 200, a microwave open-ended coaxial sensor 226 may be added to the probe in FIG. 1. A block diagram of only the microwave coaxial sensor and corresponding system elements, in accordance with an embodiment of the present invention, is illustrated in FIG. 2B. In an aspect of the present invention, a microwave open-ended coaxial sensor in the immersion probe may gather the additional flow-mixture permittivity-conductivity data at a selected measurement frequency or frequencies. The microwave open coaxial cable sensor 226 may be coupled to a microwave reflectometer or a spectrometer 224 in order to take microwave dielectric spectroscopy measurements. These measurements may be taken by utilizing the frequency dependence of the dielectric dispersion of various mixtures (e.g., water-salt or water-inhibitor) and different concentrations of those mixtures.

As shown in FIG. 2B, the microwave coaxial cable sensor 226 has, in an aspect of the present invention, an open ended aperture which is flush mounted to the flow gap 214 of the immersion probe. The open-ended aperture of the microwave coaxial sensor 226 may be in direct contact with the flow. As shown in FIG. 2B, for example, the microwave coaxial sensor 226 is in contact with the liquid layer 234 of the multiphase flow. The liquid layer 234 is shown including entrained gas bubbles, which often occurs in the multiphase flow. The microwave coaxial sensor 226 includes an inner conductor that has an outer radius a and an outer conductor, which has an inner radius b. The microwave coaxial sensor 226 includes an insulator, which is thermally and electrically stable, such as ceramics or glass. In one embodiment, the insulator is Borosilicate 7070, the inner conductor is Tungsten, the outer conductor is Inconel. The insulator has a dielectric constant $\in_L$. The selection of a, b, and $\in_L$ determines the characteristic impedance $Z_o$ of the microwave coaxial cable sensor 226 used in the immersion probe. In an embodiment of the present invention, the sensitivity depth of a coaxial sensor is roughly the same as the inner radius b of its outer conductor.

In an embodiment of the present invention, a reflectometer is used to both send the microwaves to the coaxial cable sensor and receive the reflected microwaves from the multiphase flow to determine a reflection coefficient that is a measure of the mismatch of the impedances between the sensor and the fluid. The reflectometer 224 can be of a single microwave frequency, such as 2 gigahertz (GHz), or of a range of frequencies, such as from a few hundred of megahertz (MHz) to a tens of GHz (or to THz range). This range of frequency is selected to perform dielectric spectroscopy and/or to cover a wide conductivity range expected in the water of the multiphase flow. In one embodiment two unidirectional couplers are utilized to provide an incident (transmitted) signal and a reflected (received) signal. In another embodiment, one bidirectional coupler is utilized to for both signals. With an appropriate frequency down-conversion to an intermediate-frequency range (MHz or kHz), the two microwave signals are recorded by the reflectometer 224, band-pass filtered, amplified and analog-to-digital (ADC) converted. A processor reconstructs the amplitude and phase of both the incident and reflected signals to determine the absolute amplitude attenuation and phase-shift of the reflected signal when compared to the incident signal.

The aforementioned measured signals (i.e., microwaves) of the incident and reflected signals can then be utilized to derive the complex reflection coefficient $\Gamma$ at the probe sensor aperture (i.e., the open end) of the multiphase flow. An apparent reflection coefficient $\rho$, not $\Gamma$, is actually measured by the reflectometer connected to the microwave coaxial sensor, but related to $\Gamma$ through an appropriate equation. The reflection coefficient $\Gamma$ is a measure of the mismatch between the microwave coaxial sensor 226 characteristic impedance $Z_o$ and its aperture fluid impedance $Z_C$. The analytical equation for the coefficient is:

$$\Gamma=(Z_C-Z_o)/(Z_C+Z_o)$$

With these measurements, the real and imaginary parts of the fluid complex permittivity ($\in'$, $\in''$) can be determined. The complex permittivity measure is related to the effective conductivity and dielectric properties of the liquid layer 234 mixture in the multiphase flow. In a simplistic case, the derived complex permittivity is analytically represented as:

$$\in^* = \in' - j\in''$$

where, $$\in^* = (1/j\omega Z_o C_o)(1-\Gamma/1+\Gamma) - C_f/C_o$$

$C_o$ and $C_f$=capacitance parameters characterizing the probe inner and outer fringe capacitance.

With the measured complex permittivity, the permittivity-conductivity ($\in_m$, $\sigma_m$) of the flow mixture at selected frequencies can be determined through the following analytical equation:

$$\in^* = \in_m - j\sigma_m/\omega\in_o$$

In an embodiment of the present invention, the volume fraction (X) of the hydrate inhibitor, the oil fraction ($\alpha_{coil}$) in water (hence the WLR) and the water salinity (s) may be determined through LUT mapping as illustrated in FIG. 2A, given measured conductivities ($\sigma$) and permittivities ($\in$) and optical absorptions (OD($\lambda$)) of known salt species and inhibitors, and oils, at known pressures (p) and/or temperatures (T). In an embodiment of the present invention, analysis of measurement sensitivity to changes in the water properties can be performed. For example, with the percentages of the inhibitors and/or salt content in the water known, the aforementioned look-up tables can be utilized to determine the changes in the water absorption OD calculated from spectra peaks, and the changes in the permittivity-conductivity, as can also be determined through the spectral analysis performed on the IR or UV/IR measurements and on the microwave measurements, respectively. As previously discussed, determining the correct salinity of the water is important, as it not only causes noted changes in the optical absorption peaks as well as in the permittivity-conductivity values, but also provides indication of reduced hydrate forming tendencies, which allows for lower dosages of inhibitor.

Figure 3B:
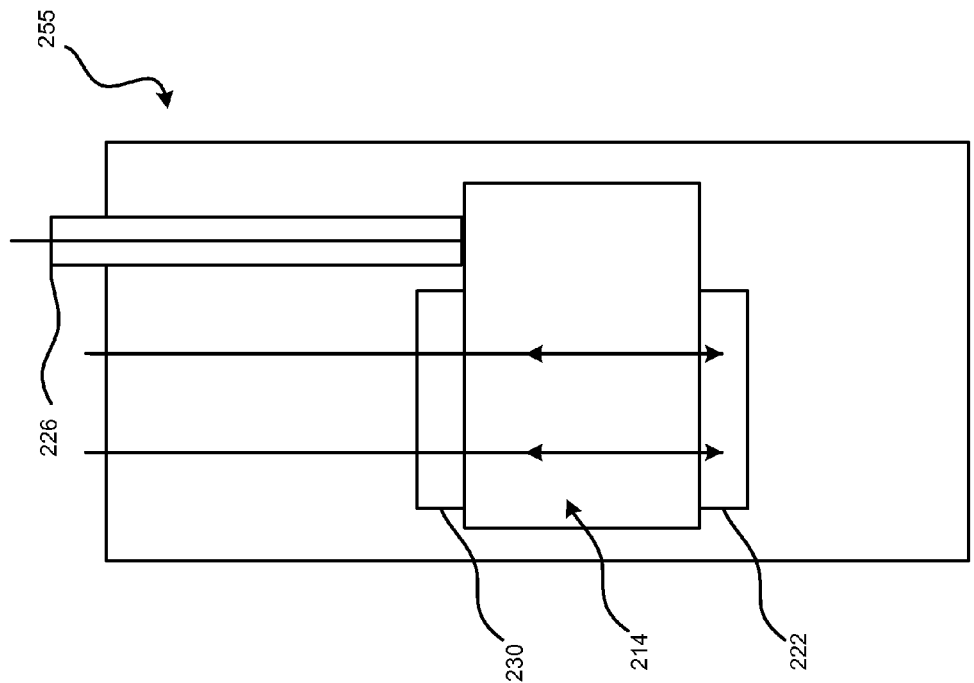
FIG. 3B provides a configuration for an immersion probe having a double optical radiation path and a microwave coaxial sensor, in accordance with an embodiment of the present invention.
Figure 3A:
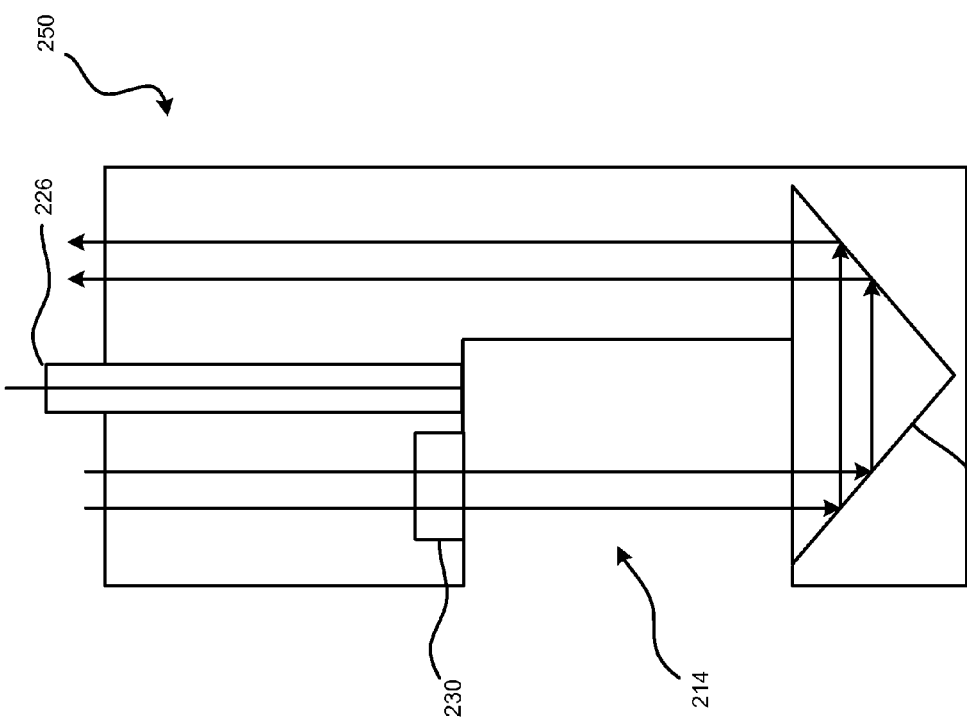
FIG. 3A provides a configuration for an immersion probe having a single optical radiation path and a microwave coaxial sensor, in accordance with an embodiment of the present invention.

Referring now to FIGS. 3A-3B, in an embodiment of the present invention, a single-path probe 250 and a double-path probe 255 are illustrated as variations of immersion probes. As previously discussed, these immersion probes 250, 255 may be utilized to measure hydrate inhibitor content in a primarily aqueous sample of water and oil in a gas-condensate well. The single-path probe 250 includes a microwave open coaxial sensor 226 located between the transmitted and reflected light paths of the IR and/or UV radiation. The sensor opens into the flow gap 214, proximate to the optical window 230 of the immersion probe, in order to measure mixture permittivity ($\in$) and mixture conductivity ($\sigma$) of liquid passing through the flow gap 214. Accordingly, microwaves are transmitted into the flow gap 214 and the complex permittivity of the flow ($\in^*=\in'-j\in''$) may be measured, allowing for the permittivity and conductivity to be calculated (e.g., $\sigma \sim 2\pi f\in''$), with a known operating frequency or frequencies being provided by the microwave radiation source. The frequency range of microwaves range from about 300 megahertz (MHz) to 300 gigahertz (GHz). In certain aspects, the range utilized is between 300 MHz and 30 GHz, which may be produced by low-power solid-state devices such as a field effect transistor, tunnel diodes.

FIG. 3B provides an alternate configuration for an immersion probe, including an enclosed flow gap 214 and double radiation path, in accordance with an embodiment of the present invention. The double-path probe 255 includes an optical window 230, a reflective element 222, and a microwave open coaxial sensor 226. In this exemplary embodiment, the microwave open coaxial sensor 226 opens into the flow gap 214 in the vicinity of the optical window 230. The flow gap can be any a range of 0.5 millimeters (mm) to 5 mm, preferable larger than the sensitivity depth of the microwave coaxial sensor 226. When using a combined probe, such as a probe utilized for measuring the content of each phase, a smaller gap, such as 1 mm may be used. However, the gap size should be large enough so that a good sample of the multiphase flow is able to pass through the gap without any hold-up due to the gap. In some embodiments, the gap can extend across the diameter of the pipe. However, in such embodiments, the accuracy of the measurements may decrease as the radiation is sent across a larger portion of the multiphase flow and can scatter due to presence of gas bubbles and/or liquid droplets, causing a large attenuation with an apparent optical density (OD) beyond the linear dynamic range of a spectrometer.

In an embodiment of the present invention, with the immersion probe 250, 255, direct characterization of broadband NIR spectra in pure water-alcohol mixtures may be utilized to determine curve-fitted estimates for derivation of inhibitor concentration with known types of alcohol (i.e., inhibitors) through look-up tables. Similarly water-salt (e.g., NaCl, KCl) solutions may be determined through NIR spectroscopy in order to aid in controlling inhibitor dosage, or injection rate by factoring in the lower hydrate forming tendency and the water absorption peak offset due to increased water salinity. As previously mentioned, high concentrations of salts within water allow for a decreased inhibitor injection rate.

Alternative embodiments, as previously discussed, can measure the inhibitor content through the microwave open coaxial sensor 226 to determine the complex permittivity of the concentration from which water conductivity and/or permittivity may be derived. Such embodiments can be useful when the flow is known to include both water-salt and water-alcohol and/or other constituents. Microwave frequency dielectric spectroscopy can then be performed in order to determine the inhibitor concentration based on the frequency dependence of dielectric dispersion and absorption. Combined NIR spectroscopy and dielectric spectroscopy can be used to determine the properties of a multiphase-flow containing multiple constituents, such as hydrate-inhibitor fraction in water, oil fraction in water (hence the WLR) and the water salinity. With the amount of water constituents known, a more accurate water-cut and water flow rate measurement can then be determined.

Figure 4:
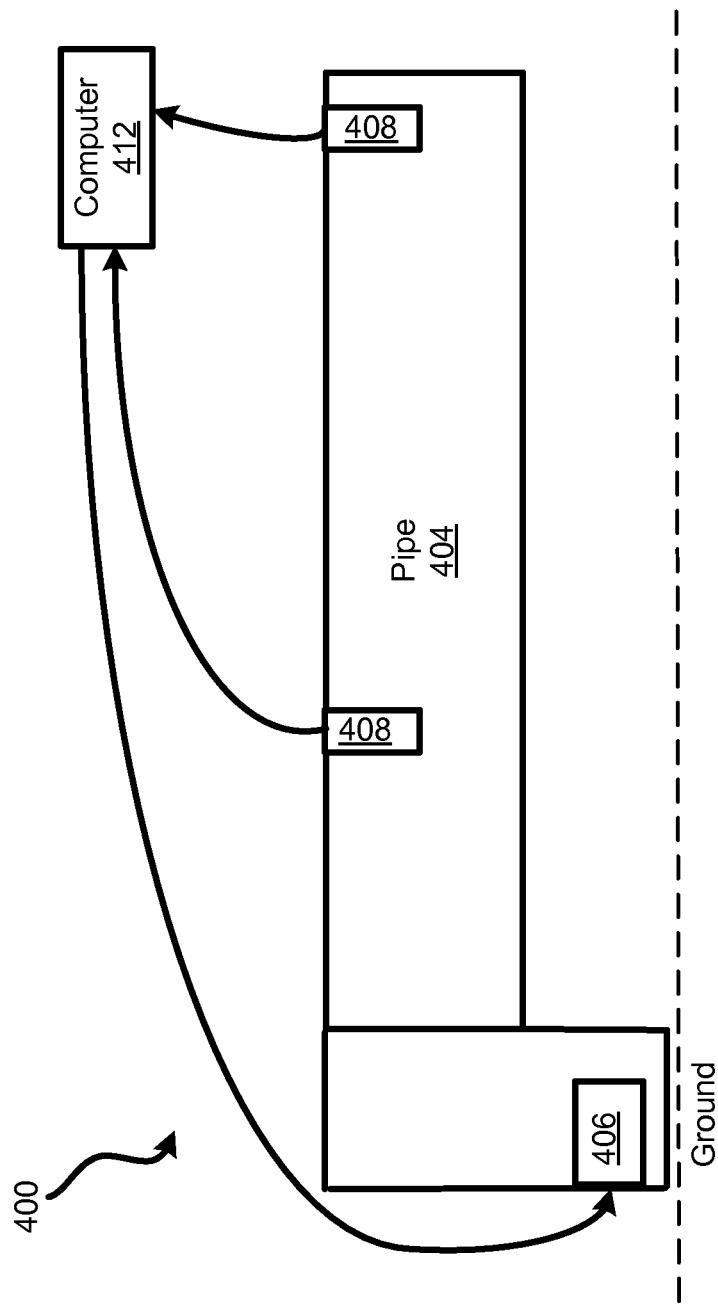
FIG. 4 provides an instrumented hydrate-inhibitor injection system including a plurality of immersion probes, in accordance with an embodiment of the present invention.

Referring now to FIG. 4, in accordance with an embodiment of the present invention, the aforementioned immersion probes 408 variations may be a part of a system 400 in which the measured water-cut, water salinity and hydrate-inhibitor fraction are used to automatically determine the inhibitor injection rate and perform any adjustments needed to the injection pump 406. In this exemplary embodiment, the system 400 includes two immersion probes 408, an injection pump 406 and a computer 412 interfaced to them. The pipe 404 delivering hydrocarbons from a well can be subsea, on surface or downhole; the pipe 404 can be horizontal, vertical or inclined. The immersion probes 408 can be any permutation of single-path or double-path probe 250, 255 configurations; they can be a long distance apart, for instance, one near a subsea wellhead for early water detection and one further downstream the pipeline nearer to the injection pump. Feedback from the immersion probes 408 is interpreted by the computer 412 to determine proper control signal for the injection pump 406 to adjust inhibitor dosage. In addition, the system 400 may be modified to be utilized in a downhole tool to monitor water and/or oil contamination in the Schlumberger™ Modular Formation Dynamics Tester (MDT) flowline.

Additionally, the nature of some crude oil and the likelihood of sediment being a part of the multiphase flow provides harsh conditions in which the immersion probe can be located. In an aspect of the present invention, the probe may be placed at a pipe location where the liquid tends to be well mixed and solids deposition is least likely. In an aspect of the present invention, the fluid-contacting window surface of immersion probe optical sensor and/or microwave sensor surface may be coated with a hydrophilic coating preferential for water-property detection, and/or a self-cleaning coating. Other means of cleaning the windows or the surface of the optical sensors and/or microwave sensors may be used, such as acoustic means. The use of such acoustic means is further discussed in commonly owned U.S. Pat. No. 7,804,598, which is hereby incorporated by reference in its entirety. In an aspect of the present invention, the housing of the immersion probe is designed to withstand high temperatures and high pressures, providing the best possible protection to the sensors and conduits which are within it. The sensors and conduits can additionally be protected, such as through insulators that provide a better medium through which the radiation (e.g., IR and microwave) can be transmitted.

Figure 5:
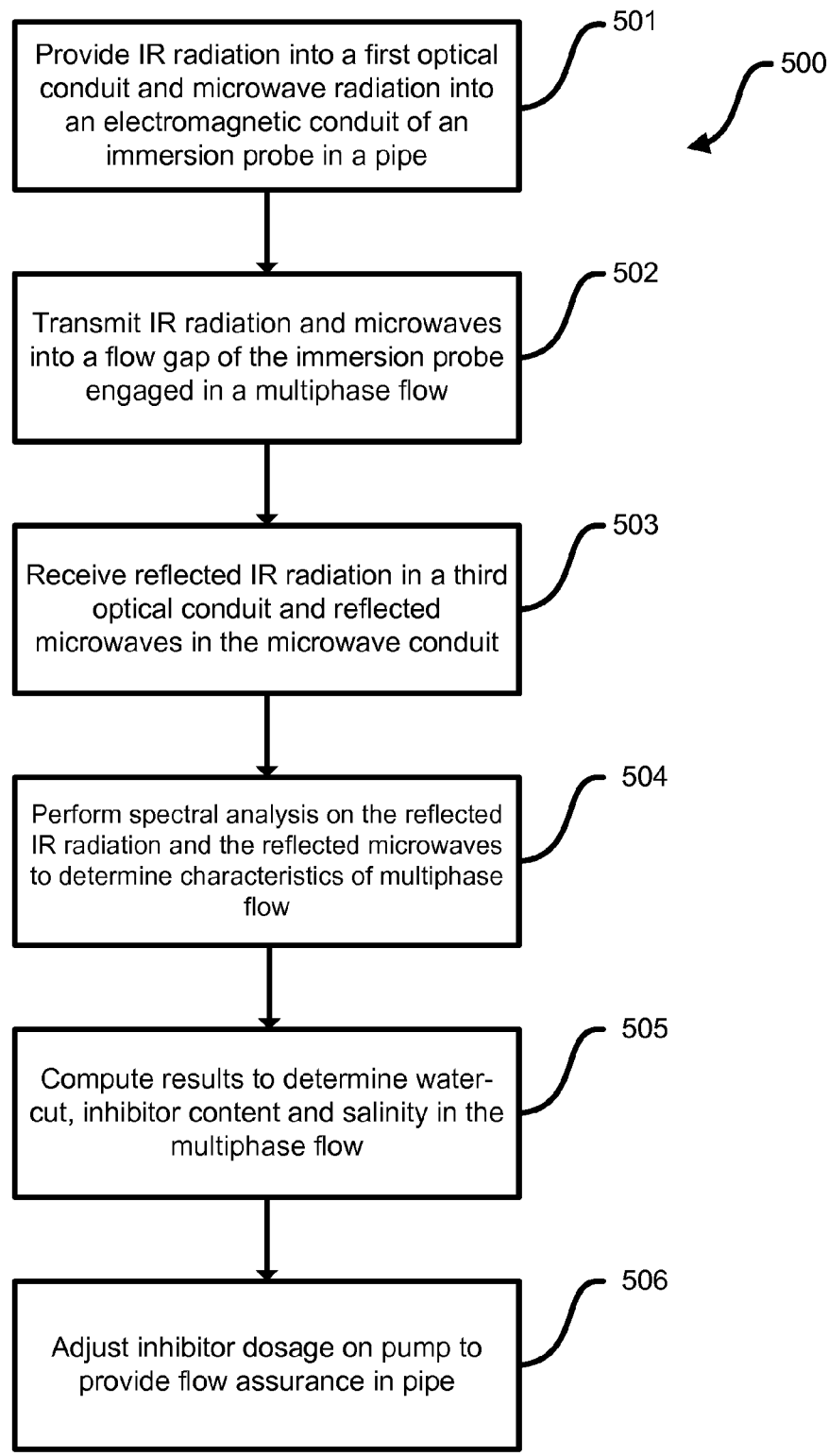
FIG. 5 provides a flow chart describing adjustment of an inhibitor dosage, in accordance with an embodiment of the present invention.

FIG. 5 provides a flowchart of an exemplary method, in accordance with an embodiment of the present invention, for adjusting inhibitor dosage, which may be used in the systems 400 in FIG. 4 and will be described with reference primarily thereto. The system 400 includes a feedback loop having one or more immersion probes 408 located within a well or an extraction pipe 404. The immersion probes 408 can be located at different points of the well or extraction, bypass, or sampling pipe 404 to measure variations in content levels through use of both infrared and microwave radiation. The flow in pipe 404 can be spun to centrifugally force the liquid toward an inner surface of the pipe with gas tending to be in the center of the pipe 404. The probes can be located in the vicinity of the pipe inner wall to measure the properties of the liquid-rich flow, or located in the vicinity of the pipe center to measure the properties of the gas-rich flow.

In step 501, radiation sources are coupled to the immersion probe 408 to provide the infrared and microwave radiation to transmitting fiber optic bundles, optics (e.g., optical window) and a microwave coaxial line, respectively. In step 502, the two types of radiation are transmitted into a flow gap 214 on the immersion probe 408. The flow gap 214 operatively engages the multiphase flow 104 within the pipe 404, preferably in a liquid-rich part of the pipe if the properties of water (hydrate-inhibitor fraction, salinity, WLR) are the main interests of the measurement. Accordingly, at least a portion of the infrared radiation passes through the multiphase flow 104 by means of the flow gap 214 and to a second end of the immersion probe 408, where a reflective element 222 is positioned.

In step 503, the reflective element 222 is utilized to reflect the infrared radiation to receiving optics and a fiber optic bundle. The microwave radiation is absorbed, reflected, or dispersed by the flow in the flow gap 214 and the reflected portion is collected in the microwave open coaxial sensor. In step 504, the immersion probe 408 provides measurements to an infrared spectral analyzer and a microwave reflectometer to determine the characteristics of the multiphase flow. These analyzed results are then sent to a computer 412, where analysis is performed. These measurement results (i.e., infrared absorption OD and microwave permittivity and/or conductivity) can then be used as inputs to the lookup tables 200 in comparison with prior established data, or by appropriate mathematical interpolation, in order to track the changes of water phase properties in terms of the volume fraction of an inhibitor in water, water-cut and water conductivity. Tracking these changes allows for proper calibration measurement of the optical absorption properties of water in the system, which, in turn, aids in determining other properties of the system such as water-cut, inhibitor concentrations, water flow rates and salinity in multiphase flows 104.

In step 505, with the water-cut of the mixture known through use of the immersion probes 408 and the aforementioned methods, the water flow rate is to be determined within the well pipe. If the water flow rate is known, the amount of inhibitor needed for injection to prevent hydrate formation may be determined, together with the measured pressure, temperature and water salinity. By measuring the multiphase flow 104 continuously over a period of time, the increase of water cut, salinity and other properties within the flow can be measured, allowing for the proper adjustment of the injection rate of the inhibitor as necessary over time. Accordingly, in step 506, the inhibitor dosage is adjusted if necessary. For example, if the multiphase water rate of the well is increasing, the computer 412 can determine that larger amounts of inhibitor needs to be injected to the well as hydrate may be beginning to form.

In another embodiment, ultraviolet radiation can also be utilized in the immersion probe in addition to IR radiation to provide an improved water-cut measurements for the multiphase flow 104, when oil and/or gas fraction is high in the flow gap. Some embodiments may use an impact pressure sensor and/or an ultrasound sensor with the immersion probe 408 to further refine measurement in the liquid flow rate. Water flow rate may be inferred from an independently measured liquid flow rate and the immersion-probe measured water cut.

If it is determined that the water flow rate is increasing and that hydrate may be beginning to form, the computer 412 communicates an increase in the amount of inhibitor being injected into the well to a pump 406. The pump 406 may be located within proximity to the well and can be controlled by the computer 412.

Utilizing the current known inhibitor injection rate and the measured inhibitor content fraction in water through the use of immersion probe 408, in an aspect of the present invention, the water flow rate may be determined as the inhibitor injection volume rate and the measured inhibitor volume concentration may be utilized as a tracer. This calculation is exemplified in the following equation:

$$\text{Water flow rate} = \text{Inhibitor volume injection rate} * \left( \frac{\text{Injected inhibitor concentration volume}}{\text{Measured inhibitor volume concentration}} - 1 \right)$$

Thus, the immersion probe 408 may measure hydrate inhibitor content within the liquid flow for multiphase flows 104 in which inhibitor injection and regulation thereof is necessary. Furthermore, the determination of water salinity and inhibitor content, in accordance with an embodiment of the present invention, provides additional correction for measurements of WLR with microwave, NIR and/UV spectroscopy as conductivity-permittivity, optical density (absorption) is markedly affected by both. Finally, in accordance with an embodiment of the present invention, determination of the water flow rate and salinity allows for a more efficient and effective inhibitor injection rate to be utilized within the system. Furthermore, in accordance with other embodiments of the present invention, the determination of the water flow rate and water salinity (knowing salt species) allows for a more efficient and effective corrosion and/or scale inhibitor injection rate to be utilized.

While the principles of the disclosure have been described above in connection with specific apparatuses and methods, it is to be clearly understood that this description is made only by way of example and not as limitation on the scope of the disclosure.

What is claimed is:

1. A method for dosing a hydrate inhibitor into a multiphase flow from a natural gas or oil well, the method comprising:
   transmitting one or more types of radiation into the multiphase flow through a flow gap located on an immersion probe, wherein at least a portion of the immersion probe is located within the well or within a pipe conveying the multiphase flow;
   measuring the one or more types of radiation received from the multiphase flow;
   collecting a first data related to the properties of the multiphase flow, wherein the first data includes the measurements of the one or more types of radiation received from the multiphase flow;
   analyzing the first data;
   communicating the first data to a processor, wherein the processor is configured to:
      determine water salinity of the multiphase flow from the first data;
      determine the amount of hydrate inhibitor in the multiphase flow from the first data;
      determine a dosage of the hydrate inhibitor from the water salinity of the multiphase flow and the amount of hydrate inhibitor in the multiphase flow; and
      set the dosage of the hydrate inhibitor on a pump; and
   utilizing the pump on which the dosage is set to inject the dosage of hydrate inhibitor into the well or the pipe conveying the multiphase flow.

2. The method of claim 1, wherein the processor is further configured to:
   compare the first data to a second data;
   monitor changes between the first data and the second data; and
   modify the dosage of the hydrate inhibitor according to the changes in the first and the second data.

3. The method of claim 2, wherein the second data includes known tables relating to the absorption spectra of optical density, multi-frequency conductivity and the permittivity of water containing contaminants, wherein the contaminants include one or more of salts, hydrate inhibitors, and oils.

4. The method of claim 2, wherein the second data is data related to the properties of the multiphase flow recorded at a time prior to the collection of the first data.

5. The method of claim 1, wherein the processor is further configured to:
   calculate a water flow rate from the first data and the dosage or injection rate of the hydrate inhibitor.

6. The method of claim 1, wherein the processor is further configured to:
   calculate a water flow rate from the first data and a flow rate of a liquid phase of the multiphase flow, wherein the flow rate of the liquid phase is measured independent from the immersion probe.

7. The method of claim 1, wherein the one or more types of radiation includes infrared radiation.

8. The method of claim 1, wherein the one or more types of radiation includes microwave and/or THz-wave radiation.

9. The method of claim 1, wherein the one or more types of radiation includes ultraviolet radiation.

10. The method of claim 1, wherein the step of analyzing is performed by one or more spectrometers through spectral analysis.

11. The method of claim 1, wherein the step of analyzing the data is performed by a reflectometer through microwave dielectric spectroscopy.

12. The method of claim 1 wherein the processor is configured to determine the content of each of water, oil and hydrate inhibitor in the multiphase flow and also the water salinity of the multiphase flow.

13. The method of claim 7 wherein the one or more types of radiation include both infrared radiation and ultraviolet radiation, and the processor is configured to determine a volume ratio of water and oil in the multiphase flow.

14. The method of claim 1, wherein the one or more types of radiation includes microwave and/or THz-wave radiation which is used to measure at least one of a permittivity and a conductivity of the multiphase flow.

15. The method of claim 7 wherein the one or more types of radiation include both infrared radiation and microwave and/or THz-wave radiation which is used to measure at least one of a permittivity and a conductivity of the multiphase flow.

* * * * *